United States Patent [19]

Ishiguro et al.

[11] Patent Number: 5,211,940
[45] Date of Patent: May 18, 1993

[54] TRANSPARENT LIQUID ORAL COMPOSITION

[75] Inventors: Keiji Ishiguro, Narashino; Osamu Uotani, Chiba; Minako Seyama, Tokyo, all of Japan

[73] Assignee: Lion Corporation, Tokyo, Japan

[21] Appl. No.: 899,310

[22] Filed: Jun. 16, 1992

[30] Foreign Application Priority Data

Jun. 21, 1991 [JP] Japan ............................. 3-177225

[51] Int. Cl.⁵ .................. A61K 7/16; A61K 33/34
[52] U.S. Cl. ............................ 424/49; 424/630; 424/638
[58] Field of Search ................... 424/49-58, 424/630, 638

[56] References Cited

U.S. PATENT DOCUMENTS

| | | |
|---|---|---|
| 3,044,939 | 7/1962 | Scanlan et al. |
| 3,565,933 | 2/1971 | Vagenius. |
| 3,655,868 | 4/1972 | Vagenius et al. |
| 4,112,066 | 9/1978 | Hussein. |
| 4,490,389 | 12/1984 | Nelson et al. ............ 424/638 |
| 4,581,374 | 4/1986 | Nelson et al. ............ 252/106 |
| 4,581,379 | 4/1986 | Nelson et al. ............ 252/106 |
| 4,797,274 | 1/1989 | Miki et al. ............... 424/638 |
| 4,997,640 | 3/1991 | Bird et al. ............... 424/49 |
| 5,094,842 | 3/1992 | Riley ..................... 424/49 |

FOREIGN PATENT DOCUMENTS

| | | |
|---|---|---|
| 56-169619 | 12/1981 | Japan. |
| 56-169620 | 12/1981 | Japan. |
| 60-193910 | 10/1985 | Japan. |
| 61-37720 | 2/1986 | Japan. |
| 61-143315 | 7/1986 | Japan. |

*Primary Examiner*—Shep K. Rose
*Attorney, Agent, or Firm*—Birch, Stewart, Kolasch & Birch

[57] ABSTRACT

A transparent liquid oral composition comprises a water-soluble copper compound and an aliphatic dicarboxylic acid compound selected from the group consisting of malic acid, succinic acid, tartaric acid and water-soluble salts thereof. The composition has an excellent storage stability with maintaining its transparent appearance for a long period of time.

13 Claims, No Drawings

TRANSPARENT LIQUID ORAL COMPOSITION

This invention relates to a transparent liquid oral composition containing a water-soluble copper compound.

BACKGROUND OF THE INVENTION

It is well known that water-soluble copper compounds such as copper gluconate and copper citrate have a bad breath inhibiting effect and a dental plaque adherence inhibiting effect. Conventionally, various oral compositions having a water-soluble copper compound blended were proposed as in U.S. Pat. Nos. 3,044,939, 3,565,933, 3,655,868 and 4,112,066 and Japanese Patent Application Kokai Nos. 56-169619, 56-169620, 60-193910, 61-37720, 61-143317, 62-142109, 1-153620 and 1-153622.

However, water-soluble copper compounds are unstable in aqueous solutions and apt to form insoluble matters due to the oxidation of themselves or the reaction with other components coexistent in the aqueous solutions.

Thus, a transparent liquid oral composition having such a water-soluble copper compound blended would become turbid or produce sediments after a long-term storage because of the formation of the insoluble matters, resulting in injuring the transparent appearance of the product.

SUMMARY OF THE INVENTION

Therefore, it is an object of the present invention is to provide a transparent liquid oral composition containing a water-soluble copper compound which has an excellent storage stability without turbidity or sediment formation even after a long-term storage at a wider temperature range.

In order to attain the above object, we have studied a stable transparent liquid oral composition containing a water-soluble copper compound. As a result, we have found that by blending an aliphatic dicarboxylic acid compound selected from malic acid, succinic acid, tartaric acid and their water-soluble salts in combination with a water-soluble copper compound, there is obtained a transparent liquid oral composition having an excellent storage stability with maintaining the transparent appearance for a long period of time. More specifically, the other acid compounds such as phosphoric acid, citric acid, aspartic acid and the like except malic acid, succinic acid, tartaric acid and their water-soluble salts cannot prevent the turbidity or sediment formation in a transparent liquid oral composition containing a water-soluble copper compound. Only by using malic acid, succinic acid, tartaric acid or their water-soluble salts, the turbidity or sediment formation in a transparent liquid oral composition containing a water-soluble copper compound can be prevented even after a long-term storage at a wider temperature range of from $-5°$ C. to $50°$ C.

Therefore, according to the present invention, there is provided a transparent liquid oral composition comprising a water-soluble copper compound and an aliphatic dicarboxylic acid compound selected from the group consisting of malic acid, succinic acid, tartaric acid and water-soluble salts thereof.

DETAILED DESCRIPTION OF THE INVENTION

An oral composition of the present invention is liquid and transparent without any turbidity. The composition can be prepared as mouthwash, liquid dentifrice, Breath freshener and the like, and contains a water-soluble copper compound and the specific aliphatic dicarboxylic acid compound as essential components.

The water-soluble copper compound includes a copper organic acid salt and a copper inorganic acid salt, although a copper organic acid salt is preferably used. Examples of the water-soluble copper compounds include copper gluconate, copper citrate, copper lauroyl sarcosinate, copper formate, copper acetate, copper propionate, copper butyrate, copper lactate, copper oxalate, copper phytate, copper tartarate, copper malate, copper succinate, copper malonate, copper maleate, copper benzoate, copper salicylate, copper aspartate, copper glutamate, copper fumarate, copper glycerophosphate, sodium copper chlorophyllin, copper chloride, copper fluoride, copper sulfate, copper fluorosilicate, copper nitrate, copper fluoroborate and copper iodate. Among them, copper gluconate and copper citrate are preferred.

The water-soluble copper compound is blended in the composition in an amount of 0.00001 to 2% by weight, more preferably 0.001 to 0.5% by weight of the composition.

The aliphatic dicarboxylic acid compound used in the present invention is selected from malic acid, succinic acid, tartaric acid and their water-soluble salts such as alkali metal salts (sodium salts, potassium salts, etc.). They are used singly or in combination.

The aliphatic dicarboxylic acid compound is blended in an amount of 0.001 to 5% by weight, more preferably 0.003 to 2% by weight of the composition. Less than 0.001% by weight would cause the turbidity or sediment formation. Over 5% by weight may adversely affect the taste of the composition.

The liquid oral composition of the present invention should preferably have a pH of 4 to 8, more preferably 4.5 to 6 from the point of effectively exerting the bad breath inhibiting effect of a water-soluble copper compound blended.

The liquid oral composition of the present invention may further contain any conventional ingredients depending upon the type and purpose of the composition. For example, a mouthwash is prepared by blending, in addition of the above two essential components, a humectant (usually in an amount of 0.1 to 20% by weight of the composition), a surface active agent (usually in an amount of 0.1 to 5.0% by weight of the composition), a sweetener (usually in an amount of 0.0001 to 1.0% by weight of the composition), and a preservative (usually in an amount of 0.0001 to 1.0% by weight of the composition), and solubilizing the ingredients into water.

Examples of the humectant include glycerin, sorbitol, propylene glycol and polyethylene glycol. Examples of the surface active agent include sodium lauryl sulfate, sodium $\alpha$-olefin sulfonate, N-acyl sarcosinate, N-acyl glutamate, sucrose fatty acid ester, alkanol amide, polyoxyethylene hydrogenated castor oil and polyglycerin fatty acid ester. Examples of the sweetener include sodium saccharin, stevioside, p-methoxycinnamic aldehyde and perilartin. Examples of the preservative include parahydroxybenzoate and sodium benzoate.

An effective ingredient such as fluorine compounds, aluminium hydroxy allantoinate, hinokitiol, ascorbic acid, lysozyme chloride, glycyrrhizic acid and its salts, sodium chloride, dl-α-tocopherol acetate, iso-propyl-methylphenol chlorhexidine salts, cetylpyridinium chloride, azulene, glycyrrhetinic acid, aluminum lactate, hydroxamic acid and its derivatives, dextranase, mutanase, benzethonium chloride, trichlorocarbanilide, zinc citrate, Japanese Angelica extract, and extracts from clove, scutellaria and safflower may also be blended in the composition. A flavor such as l-menthol, carvone, anethol, spearmint oil and peppermint oil and a coloring matter may be added.

EXAMPLE

Examples of the present invention are given below by way of illustration and not by way of limitation. In Examples, all percents are by weight.

EXAMPLE 1

Sample solutions shown in Table 1 were prepared by using copper gluconate as a water-soluble copper compound. The sample solutions were left in a thermostat controlled to a constant temperature of 50° C., 40° C., 25° C. or −5° C. for three months and thereafter the change of appearance of the test solutions was visually evaluated by the following criteria. The results are shown in Table 1.

Evaluation ○ : A sample solution was transparent and not turbid, and had no sediments. x: A sample solution was turbid or had sediments.

TABLE 1

| Number | 1 | 2 | 3 | 4 | 5 | 6 | 7 | 8 |
|---|---|---|---|---|---|---|---|---|
| Copper gluconate | 0 | 0.1 | 0.1 | 0.1 | 0.1 | 0.1 | 0.1 | 0.1 |
| Phosphoric acid | 0 | 0 | 0.1 | 0 | 0 | 0 | 0 | 0 |
| Citric acid | 0 | 0 | 0 | 0.1 | 0 | 0 | 0 | 0 |
| Aspartic acid | 0 | 0 | 0 | 0 | 0.1 | 0 | 0 | 0 |
| Malic acid | 0 | 0 | 0 | 0 | 0 | 0.1 | 0 | 0 |
| Succinic acid | 0 | 0 | 0 | 0 | 0 | 0 | 0.1 | 0 |
| Tartaric acid | 0 | 0 | 0 | 0 | 0 | 0 | 0 | 0.1 |
| Flavor | 0.2 | 0.2 | 0.2 | 0.2 | 0.2 | 0.2 | 0.2 | 0.2 |
| Ethanol | 10.0 | 10.0 | 10.0 | 10.0 | 10.0 | 10.0 | 10.0 | 10.0 |
| Glycerin | 5.0 | 5.0 | 5.0 | 5.0 | 5.0 | 5.0 | 5.0 | 5.0 |
| Polyoxyethylene hydrogenated castor oil | 1.0 | 1.0 | 1.0 | 1.0 | 1.0 | 1.0 | 1.0 | 1.0 |
| Sodium benzoate | 0.3 | 0.3 | 0.3 | 0.3 | 0.3 | 0.3 | 0.3 | 0.3 |
| Purified water | Balance | Balance | Balance | Balance | Balance | Balance | Balance | Balance |
| Total | 100 | 100 | 100 | 100 | 100 | 100 | 100 | 100 |
| Storage temperature | | | | | | | | |
| 50° C. | ○ | X | X | X | ○ | ○ | ○ | ○ |
| 40° C. | ○ | X | X | ○ | ○ | ○ | ○ | ○ |
| 25° C. | ○ | ○ | X | ○ | ○ | ○ | ○ | ○ |
| −5° C. | ○ | ○ | X | ○ | X | ○ | ○ | ○ |
| | | Comparison | | | | | Invention | |

As is evident from the results of Table 1, the sample solution No. 1 containing no copper gluconate neither became turbid nor produced sediments even after a long-term storage at various temperatures of from −5° C. to 50° C. On the other hand, the sample solution No. 2 having copper gluconate blended became turbid or produced sediments after a high temperature storage. Although phosphoric acid, citric acid or aspertic acid was added to the sample solution No. 2, the turbidity or sedimentation was not prevented as recognized in the results of the sample solutions Nos. 3 and 5.

Whereas, the sample solutions Nos. 6 to 8 in which malic acid, succinic acid or tartaric acid was blended with copper gluconate did not become turbid and produce any sediments even after a long-term storage at low and high temperatures of −5° C. to 50° C., and their transparent appearances were kept stably.

EXAMPLE 2

Mouthwash

| | |
|---|---|
| Copper gluconate | 0.1% |
| Malic acid | 0.03 |
| Sodium malate | 0.07 |
| Ethanol | 3.0 |
| Glycerin | 5.0 |
| Sodium saccharin | 0.008 |
| Polyoxyethylene hydrogenated castor oil | 1.0 |
| Flavor | 0.4 |
| Sodium benzoate | 0.3 |
| Water | Balance |
| Total | 100.0% |

EXAMPLE 3

Mouthwash

| | |
|---|---|
| Copper gluconate | 0.05% |
| Tartaric acid | 0.04 |
| Sodium tartarate | 0.07 |
| Ethanol | 10.0 |
| Sorbitol | 8.0 |
| Pluronic F127 | 3.0 |
| Coloring matter | 0.0002 |
| Flavor | 0.25 |
| Sodium benzoate | 0.3 |
| Water | Balance |
| Total | 100.0% |

EXAMPLE 4

Mouthwash

| | |
|---|---|
| Copper citrate | 0.1% |
| Malic acid | 0.08 |
| Ethanol | 8.0 |
| Glycerin | 10.0 |
| Polyoxyethylene hydrogenated castor oil | 1.5 |
| Methyl parahydoxybenzoate | 0.1 |
| Propyl parahydoxybenzoate | 0.05 |
| Flavor | 0.3 |
| Water | Balance |

| -continued | |
|---|---|
| Total | 100.0% |

EXAMPLE 5

Mouthwash

| Copper sulfate | 0.05% |
|---|---|
| Succinic acid | 0.06 |
| Ethanol | 1.5 |
| Sorbitol | 5.0 |
| Sodium lauryl sulfate | 0.5 |
| Methyl parahydoxybenzoate | 0.1 |
| Ethyl parahydoxybenzoate | 0.05 |
| Flavor | 0.4 |
| Water | Balance |
| Total | 100.0% |

EXAMPLE 6

Mouthwash

| Copper gluconate | 0.1% |
|---|---|
| Tartaric acid | 0.05 |
| Ethanol | 15.0 |
| Glycerin | 8.0 |
| Sucrose fatty acid ester | 2.0 |
| Sodium benzoate | 0.25 |
| Flavor | 0.3 |
| Water | Balance |
| Total | 100.0% |

EXAMPLE 7

Mouthwash (concentrated)

| Copper gluconate | 0.3% |
|---|---|
| Malic acid | 0.15 |
| Ethanol | 45.0 |
| Glycerin | 35.0 |
| Polyoxyethylene sorbitan monooleate (Tween 80) | 1.0 |
| Coloring matter | 0.002 |
| Flavor | 2.5 |
| Water | Balance |
| Total | 100.0% |

EXAMPLE 8

Breath freshener

| Copper gluconate | 0.03% |
|---|---|
| Succinic acid | 0.03 |
| Sodium succinate | 0.01 |
| Ethanol | 30.0 |
| Glycerin | 15.0 |
| Polyoxyethylene hydrogenated castor oil | 3.0 |
| Flavor | 1.0 |

| -continued | |
|---|---|
| Water | Balance |
| Total | 100.0% |

We claim:

1. A transparent liquid oral composition comprising a water-soluble copper compound and an aliphatic dicarboxylic acid compound selected from the group consisting of malic acid, succinic acid, tartaric acid and water-soluble salts thereof.

2. The composition of claim 1 wherein the water-soluble copper compound is blended in an amount of 0.00001 to 2% by weight of the composition and the aliphatic dicarboxylic acid compound is blended in an amount of 0.001 to 5% by weight of the composition.

3. The composition of claim 1, wherein the aliphatic dicarboxylic acid compound is malic acid or a water-soluble salt thereof.

4. The composition of claim 1, wherein the aliphatic dicarboxylic acid compound is succinic acid or a water-soluble salt thereof.

5. The composition of claim 1, wherein the aliphatic dicarboxylic acid compound is tartaric acid or a water-soluble salt thereof.

6. The composition of claim 1, wherein the water-soluble copper compound is a copper organic acid salt or a copper inorganic acid salt.

7. The composition of claim 1, wherein the water-soluble copper compound is selected from the group consisting of copper gluconate, copper citrate, copper lauroyl sarcosinate, copper formate, copper acetate, copper propionate, copper butyrate, copper lactate, copper oxalate, copper phytate, copper tartarate, copper malate, copper succinate, copper malonate, copper maleate, copper benzoate, copper salicylate, copper aspartate, copper glutamate, copper fumarate, copper glycerophosphate, sodium copper chlorophyllin, copper chloride, copper fluoride, copper sulfate, copper fluorosilicate, copper nitrate, copper fluoroborate and copper iodate.

8. The composition of claim 1, wherein the water-soluble copper compound is blended in an amount of 0.001 to 0.5% by weight of the composition.

9. The composition of claim 1, wherein the aliphatic dicarboxylic acid compound is in the form of a water-soluble salt selected from the group consisting of sodium and potassium salts.

10. The composition of claim 1, wherein the aliphatic dicarboxylic acid compound is blended in an amount of 0.003 to 2% by weight of the composition.

11. The composition of claim 1, wherein the pH of said composition is 4 to 8.

12. The composition of claim 1, wherein the pH of said composition is 4.5 to 6.

13. The composition of claim 1, further comprising a humectant, a surface active agent, a sweetener and a preservative.

* * * * *